(12) United States Patent
Tyrrell

(10) Patent No.: US 6,524,533 B1
(45) Date of Patent: Feb. 25, 2003

(54) DEVICE FOR COLLECTING AND DRYING A BODY FLUID

(75) Inventor: Steven P. Tyrrell, Highland Park, IL (US)

(73) Assignee: BioSafe Medical Technologies, Inc., Lake Forest, IL (US)

(*) Notice: Subject to any disclaimer, the term of this patent is extended or adjusted under 35 U.S.C. 154(b) by 0 days.

(21) Appl. No.: 09/674,407

(22) PCT Filed: Apr. 29, 1999

(86) PCT No.: PCT/US99/09479
§ 371 (c)(1),
(2), (4) Date: Oct. 26, 2000

(87) PCT Pub. No.: WO99/57559
PCT Pub. Date: Nov. 11, 1999

Related U.S. Application Data

(60) Provisional application No. 60/077,030, filed on Mar. 6, 1998.

(51) Int. Cl.[7] .............................................. G01N 33/49
(52) U.S. Cl. .................. 422/102; 422/101; 422/103; 422/61
(58) Field of Search .............................. 422/58, 61, 99, 422/102, 103; 436/165

(56) References Cited

U.S. PATENT DOCUMENTS

| | | |
|---|---|---|
| 4,987,085 A | 1/1991 | Allen et al. |
| 5,139,685 A | 8/1992 | DeCastro et al. |
| 5,208,163 A * | 5/1993 | Charlton et al. .............. 436/63 |

FOREIGN PATENT DOCUMENTS

WO 99/57559 11/1999

OTHER PUBLICATIONS

International Search Report from PCT/US99/09479.

* cited by examiner

Primary Examiner—Lyle A. Alexander
(74) Attorney, Agent, or Firm—Olson & Hierl, Ltd.

(57) ABSTRACT

A device to collect, dry and transport precise volumes of blood. A blood sample is introduced into a device through an aperture connected to a channel containing an absorbent material.

22 Claims, 7 Drawing Sheets

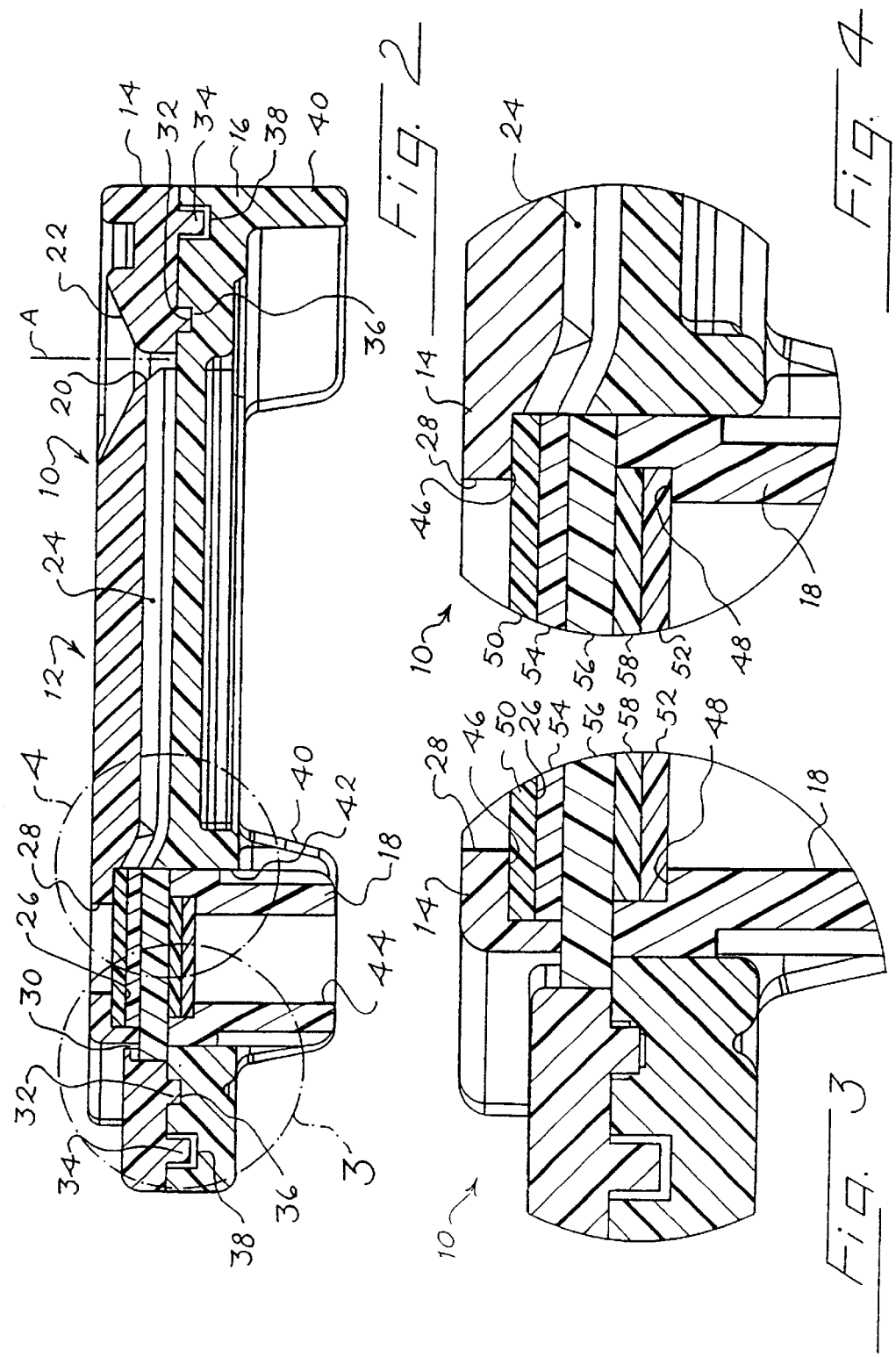

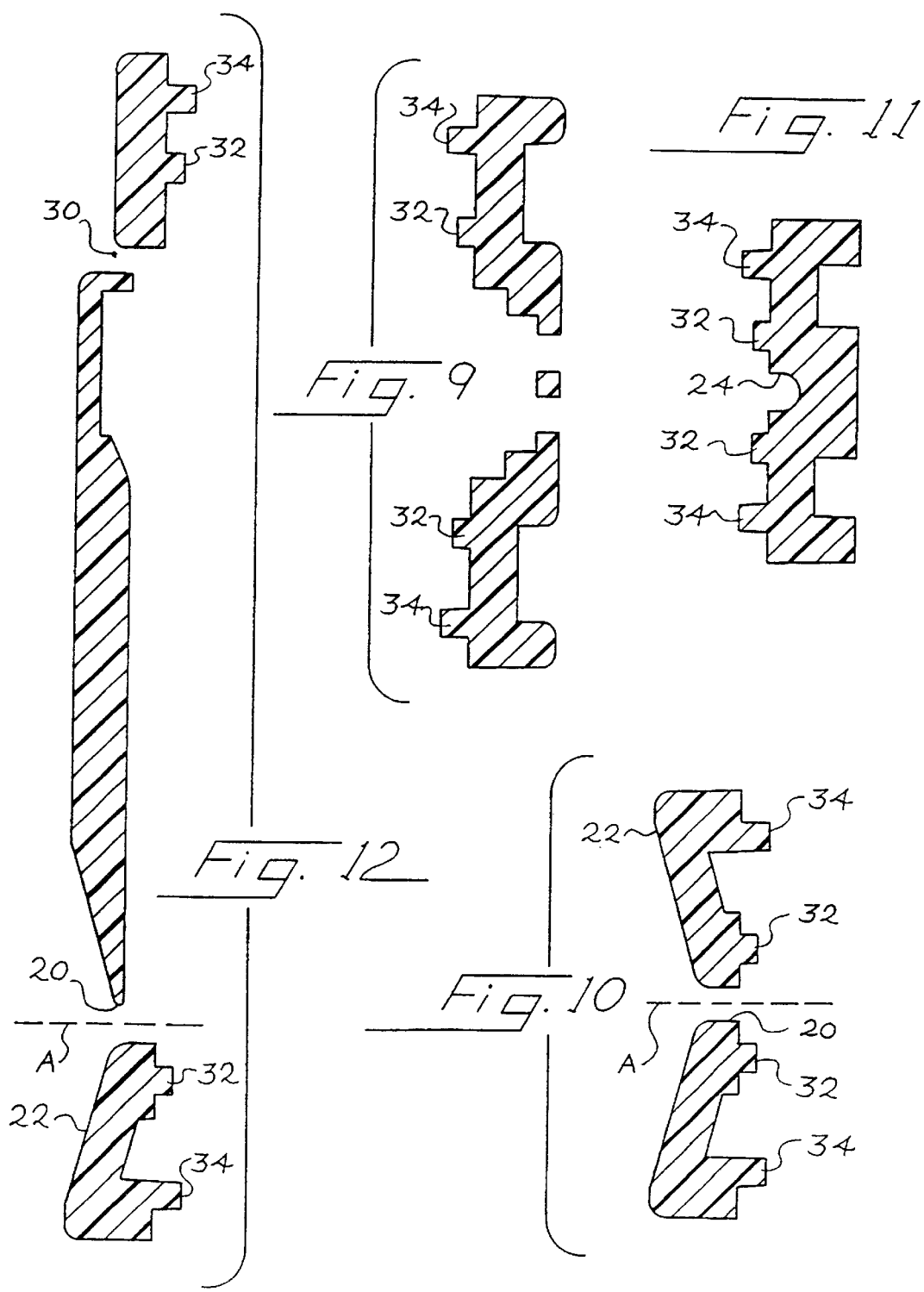

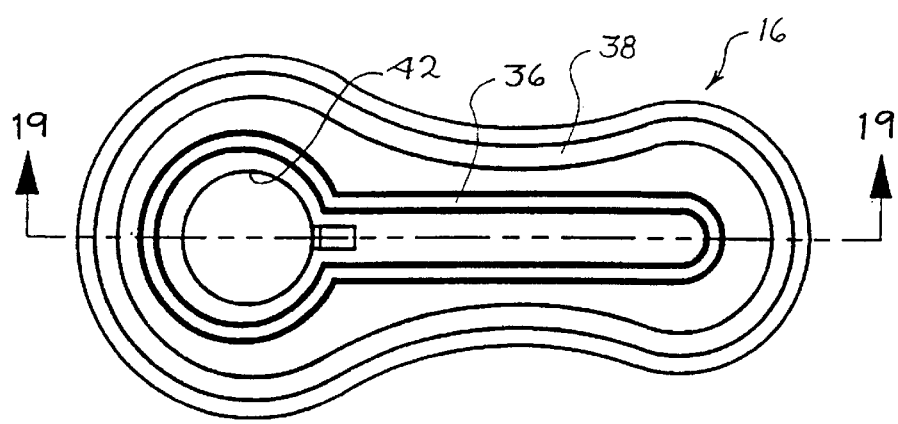
Fig. 13
Fig. 14
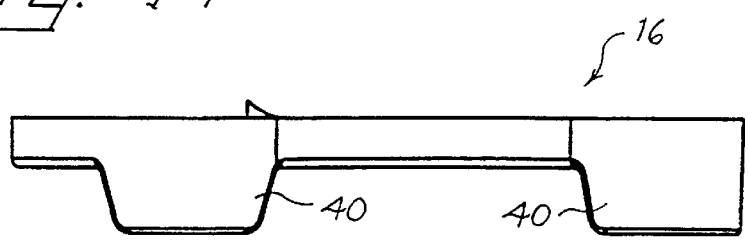
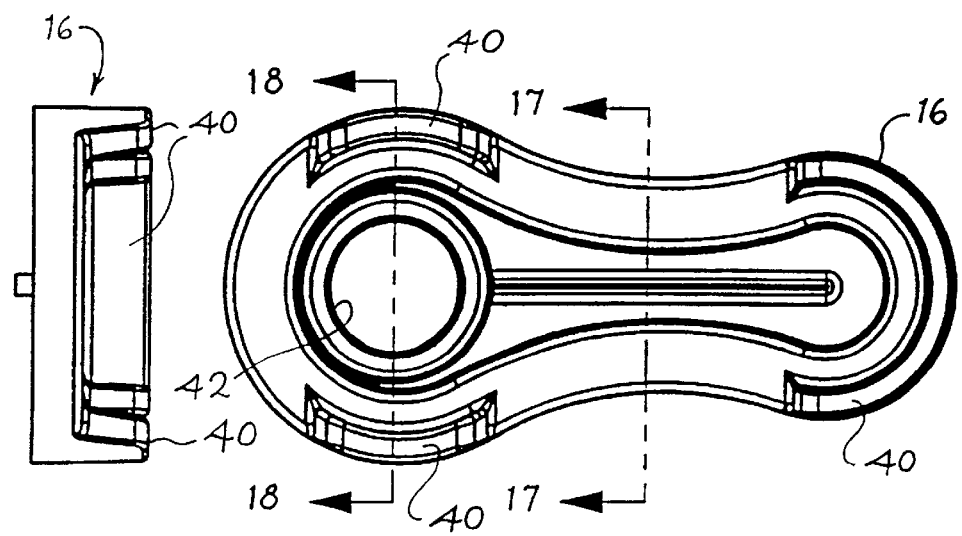
Fig. 16  Fig. 15

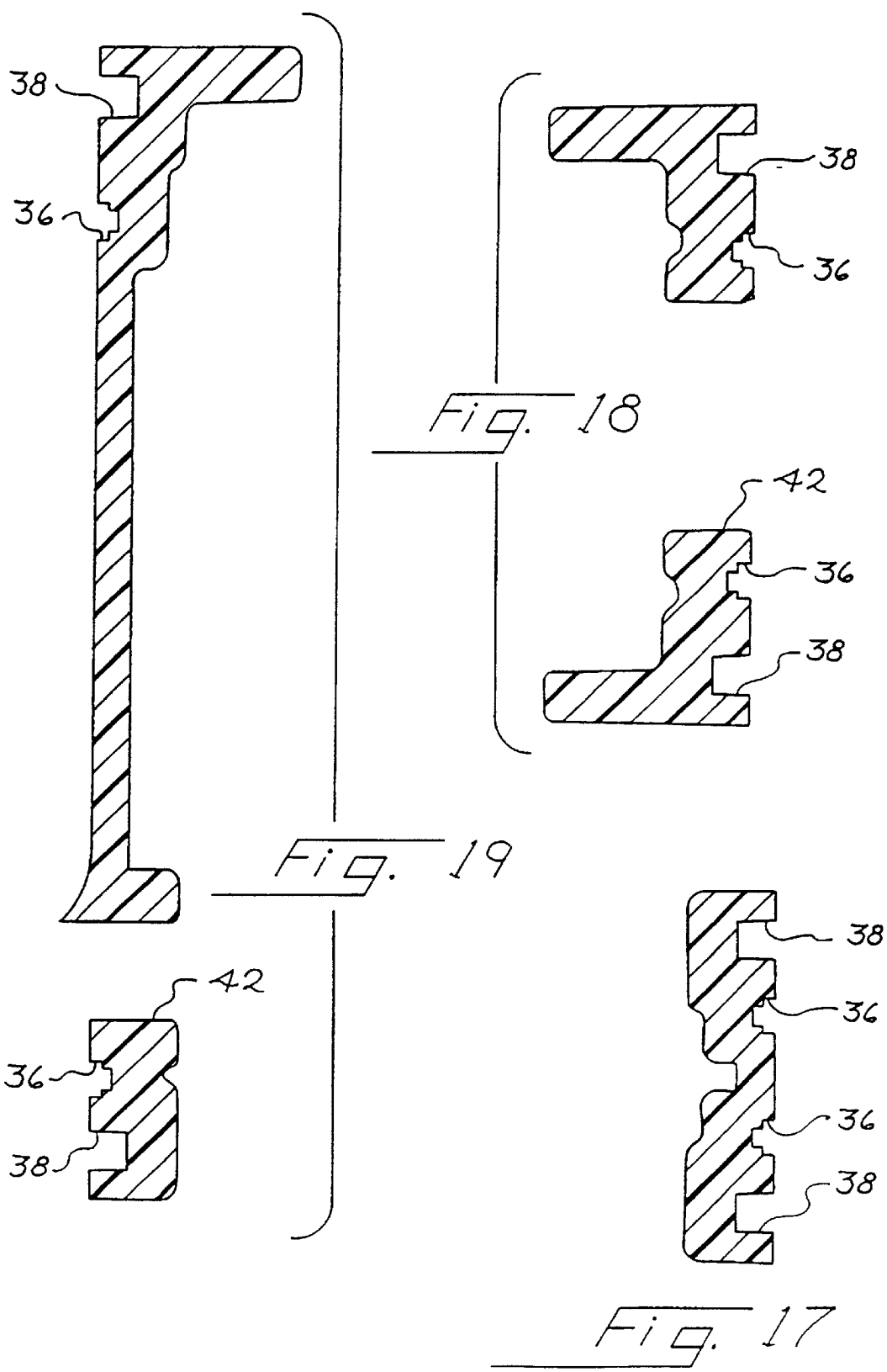

DEVICE FOR COLLECTING AND DRYING A BODY FLUID

This application claims the benefit of Provisional Application No. 60/077,030 filed Mar. 6, 1998.

FIELD OF THE INVENTION

The present invention is directed generally to the field of collecting and drying samples of body fluid such as blood. The preferred embodiments are devices for collecting and drying capillary or venous blood samples for the subsequent analytical, quantitative determination of clinical chemistry analytes.

BACKGROUND

Methods for assaying the constituents of blood are indispensable tools in the diagnosis and treatment of human disease. Analysis of dried blood is advantageous as the blood sample can be self-collected, and shipment of the blood sample to the laboratory is simplified since storage at ambient temperature and shipping through regular mail is permitted. Analysis of dried blood is further advantageous in that the sample poses a reduced risk of biohazardous exposure and the sample remaining after initial analysis can be stored in a repository for later use.

It is well known in the art that blood may be collected and dried on absorbent material for subsequent clinical assays. For example, it is well known that blood can be collected and dried on Schleicher & Schuell no. 903™ specimen collection paper and assayed for the presence of glycosylated hemoglobin (Little et al., "Collection of Blood on Filter Paper for Measurement of Glycated Hemoglobin by Affinity Chromatography", *Clin. Chem.* 32: 869–871 (1986); Little et al., "Measurement of Glycosylated Whole-Blood Protein for Assessing Glucose Control in Diabetes: Collection and Storage of Capillary Blood on Filter Paper", *Clin. Chem.* 30, 213–216 (1985)). Wet blood has also been collected and dried on Schleicher & Schuell no. 903™ paper and then assayed for the presence of prostate-specific antigen (PSA) (Hoffman et al., "assay of prostate-specific antigen from blood spotted on filter paper and application to prostate cancer screening", *Clin. Chem.* 42, 536–544 (1996)).

Another absorbent material that has been used to collect wet blood is described in U.S. Pat. No. 5,563,042, "Whole Blood Glucose Test Strip." The blood however was not dried and was assayed in its wet form for the presence of glucose (U.S. Pat. No. 5,563,042, supra).

One problem with collecting and drying blood is that the spots are not always uniform in the disbursement of whole blood/serum/whole blood cell components throughout the total volume of the matrix, leading to inconsistencies in analysis. One significant advantage of the present invention is that it allows for the collection and drying of blood samples that are of uniform volume and integrity. As a result, the analytical results are more accurate and reproducible.

Another advantage of the present invention is that once the blood sample is inside the apparatus there is a diminished risk of contamination or loss of integrity of the sample.

These and other objects of the invention will be apparent in light of the detailed description below.

SUMMARY

The present invention relates to a device for consistently collecting and drying capillary or venous blood samples of a uniform quantity and integrity. The devices described below include a housing that defines an external opening, an internal compartment, and a channel interconnecting the opening and the compartment. The compartment is bounded at least in part by porous hydrophobic sheet material and encloses absorbent material. The sheet material allows water vapor to pass while retaining liquids. The absorbent material contained in the internal compartment optionally extends into the channel. A body fluid such as blood is applied through the external opening in the housing and is then drawn into the absorbent material in the internal compartment via the channel. Once the absorbent material in the internal compartment is saturated with fluid, then no more fluid will be drawn in to the device as the capillary action of the material will cease. The water- and air-vapor permeable nature of the sheet material allows fluid to dry in the housing without disassembling the device. After the fluid sample has dried, the device is disassembled and the sample or part of the sample is analyzed for the presence of a fluid constituent. The facile nature of operating this device permits even a user untrained in the blood collection arts to prepare a defined sample size of dried body fluid such as blood for laboratory analysis. As a result, the assay results are reproducible and consistent.

These and other features and advantages of the present invention may be better understood by considering the following detailed description of certain preferred embodiments of the invention. In the course of this description, reference will be made to the attached drawings.

BRIEF DESCRIPTION OF THE DRAWINGS

Various objects, features, and attendant advantages of the present invention can be more fully appreciated as the same become better understood with reference to the following detailed description when considered in connection with the accompanying drawings, in which:

FIG. 2 is a longitudinal sectional view of a second preferred embodiment of this invention.

FIGS. 3 and 4 are enlarged sectional views of the indicated portions of FIG. 2.

FIGS. 9, 10, 11, and 12 are cross-sectional views taken along the corresponding section lines of FIGS. 5 and 7.

FIGS. 13, 14, 15, and 16 are top, side, bottom, and end views, respectively, of the lower part 16 of the device 10 of FIGS. 2 through 4.

FIGS. 17, 18, and 19 are cross-sectional views taken along corresponding section lines of FIGS. 13 and 15.

DETAILED DESCRIPTION OF PRESENTLY PREFERRED EMBODIMENTS

First Preferred Embodiment

Figure 1A:
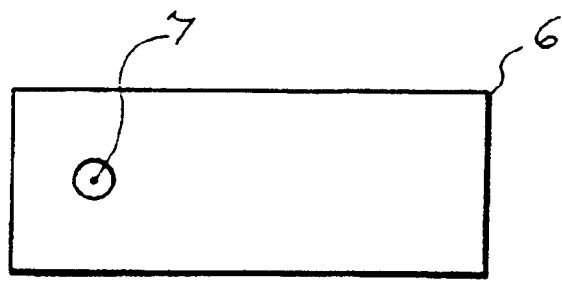
FIGS. 1(a), (b) and (c) and (d) describe component parts of a first preferred device for collecting and drying blood samples.

A preferred device for collecting and drying blood sample is illustrated in FIGS. 1(a), (b), (c), and (d).

Figure 1B:
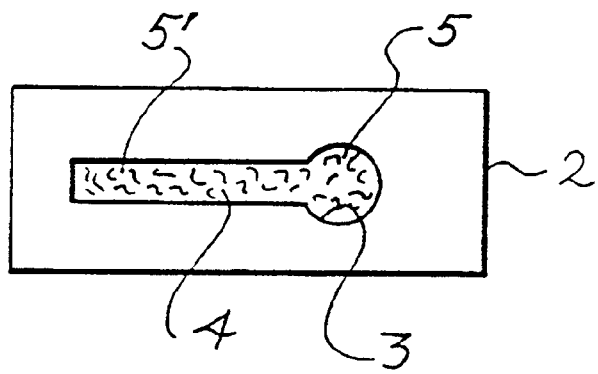
Figure 1C:
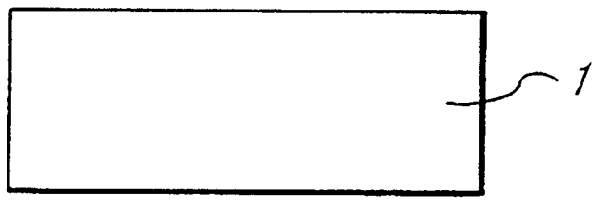

FIG. 1(c) is a base plate 1. FIG. 1(b) shows a middle plate 2 with which defines an opening 3 and a lateral channel 4. FIG. 1(a) is a top plate 6 having an aperture 7. The lateral channel 4 is filled with a strip 5', which is made of a porous hydrophilic material which will act to create a capillary draw of fluid through the sample collection disc 1. The opening 3 is filled with a sample collection disc 5, made of an absorbent material.

Figure 1D:
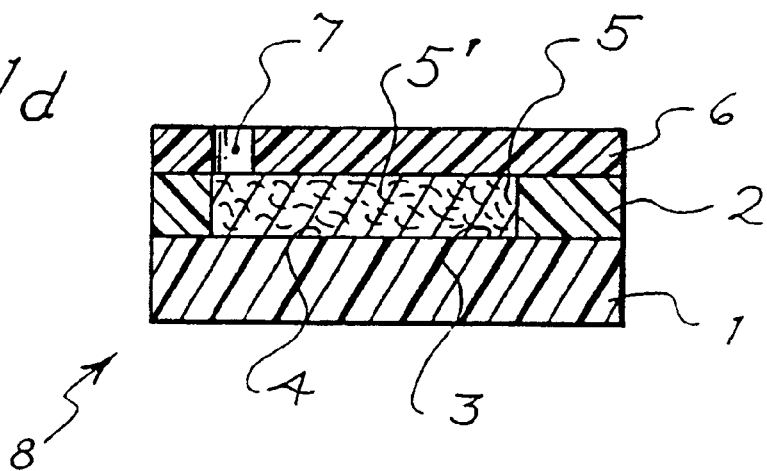
Figure 5:
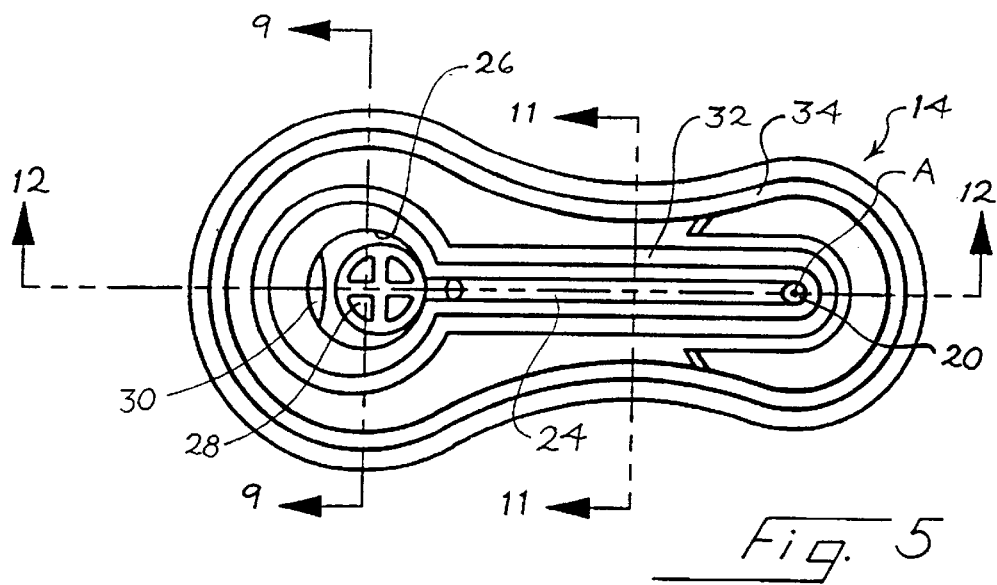
FIGS. 5, 6, 7 and 8 are bottom, side, top and end views, respectively, of the upper part 14 of the device 10 of FIGS. 2 through 4.
Figure 6:
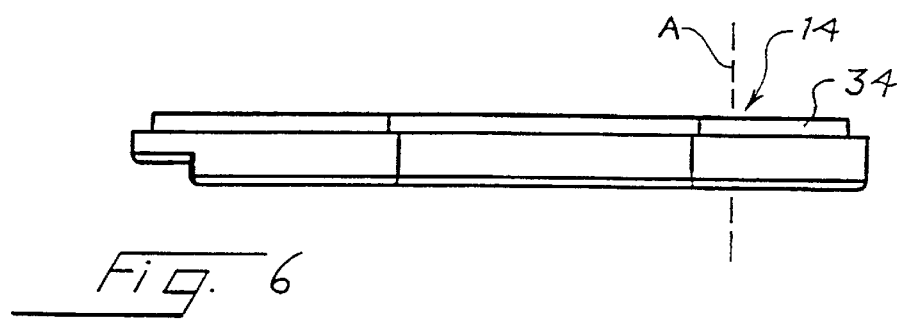
Figures 7, 8:
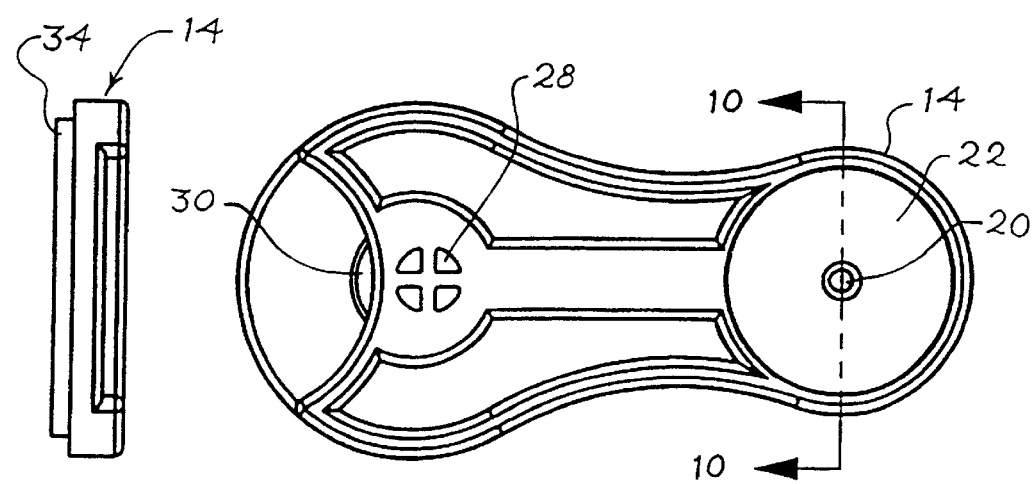

Stacking the plates on top of each other assembles the device 8 (FIG. 1(d)). The middle plate 2 (FIG. 1(b)), containing a sample collection disc 5 in the opening 3 and a strip 5' in the lateral channel 4, is placed flat on top of the base plate 1 (FIG. 1(c)). Then the top plate 6 is placed flat on top of the middle plate 2 such that the aperture 7 is directly over the lateral channel 4 containing the strip 5'. The plates may be assembled using fastening or chemical means. Those skilled in the mechanical arts will recognize a wide variety of fastening and chemical means that can serve to hold the stacked plates (top plate 6, middle plate 2, housing absorbent material and the base plate 1) together to form the assembled device 8 (FIG. 1(d)). FIG. 1(d) shows a cross sectional view of the device 8.

The strip 5' and the sample collection disc 5 should be composed of a hydrophilic medium that can uniformly absorb and distribute a fluid, such as wet whole blood. The absorbent material used for the sample collection disc 5 should allow for the covalent capture and binding of clinical chemistry analytes, and their subsequent drying and elution all the while maintaining their composition and integrity.

Those skilled in the clinical chemistry arts will recognize a wide variety of porous materials suitable as a matrix for a dried blood sample. One such material, Schleicher & Schuell no. 903™ specimen collection paper, is suitable for the collection and drying of blood samples. (See e.g., Hoffman et al., (1996), supra; Little et al., (1986), supra; Little et al., (1985), supra)., Schleicher & Schuell no. 903™ specimen collection paper is a pure cotton linter paper that was specifically designed for the collection and transport of bodily fluids. This material is well known to be suitable as a dried blood collection matrix, however, it exhibits an inherent variability in the void volume of the blood held per area, which limits its performance in accuracy and reproducibility of quantitative clinical chemistry analyte determination.

The identified material of choice is a porous hydrophilic plastic medium—Porex® Plastics 70 $\mu$m Lateral-Flow™ X-4588 (Porex Technologies Corp.; Fairburne, Ga.). This medium is a hydrophilic high-density polyethylene (HDPE) material manufactured at varying thickness and pore size specifications. For our purposes we have identified an average pore size of 70 $\mu$m and thickness of 0.021–0.029" to adequately allow the flow of whole blood through the device with adequate capture and binding of clinical chemistry analytes. The Porex® Plastics 70 $\mu$m Lateral-Flow™ material is permeable to water and air vapor, thus allowing for the uptake and drying of a capillary or venous blood of the sample collection disc 5, while it is still contained within the assembled device 8 (FIG. 1(d)). This material provides significant advantages in producing a uniform distribution and volume of blood resulting in a dried blood sample that yields a more accurate and reproducible quantitative determination of clinical chemistry analytes.

The plates, top plate 6, middle plate 2, and base plate 1, are made of a hydrophobic plastic material that does not absorb fluid. The identified material of choice is a non-porous hydrophobic plastic medium—Porex® T3 (Porex Technologies Corp., Fairburne, Ga.). This medium is an ultra-high molecular weight polyethylene (UHMW) material manufactured at varying thickness and pore size. For our purposes, we have identified an average pore size of 7 $\mu$m and thickness of 0.021–0.029" to adequately serve as a barrier to aqueous flow. The Porex® T3 7 $\mu$m material is impermeable to water and air flow, thus providing an opening 3 and a lateral channel 4 for the uptake of a capillary or venous blood sample into sample collection disc 5 and strip 5' while preventing liquid from escaping the device during the drying of blood in sample collection disc 5.

Operation Of The First Preferred Embodiment

The user (not shown) applies a blood sample (not shown) to the aperture 7. The blood sample is drawn into the device by the capillary action of the absorbent material in the channel, strip 5', and then into the sample collection disc 5. The application process is so simple that even a user untrained in the practice of blood collection and transfer may apply the sample successfully to the device. The untrained user can use the device by obtaining capillary blood from a self-administered finger stick using a finger lancet. The capillary blood that flows from the finger stick is applied at the aperture 7 of the blood collection device. The application may take place in a hospital, physician's office, health clinic, worksite health center, or even in the user's home.

Once the strip 5' and the sample collection disc 5 have absorbed the maximum void volume of the porous material, no more blood is drawn in to the device as the capillary action of the material is exhausted. Using the same sized sample collection disc for each device will ensure that the samples take up the same volume of blood, within a negligible defined range. Because the sample collection disc 5 takes up a precise volume of capillary or venous blood, the dried blood contained within the sample collection disc 5 will allow for more accurate and precise analytical determinations of clinical chemistry analytes.

The absorbent material that comprises the strip 5' and sample collection disc 5 should substantially fill the lateral channel 4 and the opening 3, respectively. This will help to prevent voids in the housing of the device and produce a more uniform sample.

When blood sample in the sample collection disc S is dry, the device is disassembled and the sample collection disc 5 is removed. The dried blood sample can be kept inside the device at ambient temperatures and sent to a laboratory for testing. The dried blood sample within the sample collection disc 5 may then be subjected to quantitative analytical determinations of numerous clinical chemistry analytes. Those skilled in the clinical chemistry arts will recognize a wide variety of assays that may be performed on dried blood samples. (See e.g., Hoffman et al., (1996), supra; Little et al., (1986), supra; Little et al., (1985), supra).

Second Preferred Embodiment

Figure 20:
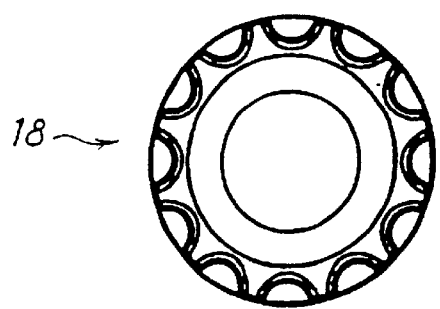
FIGS. 20, 21, and 22 are bottom, side, and top views, respectively, of the plug 18 of the device 10 of FIGS. 2 through 4.
Figure 21:
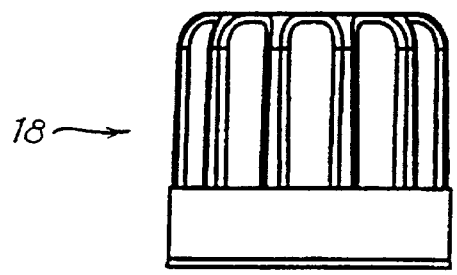
Figure 22:
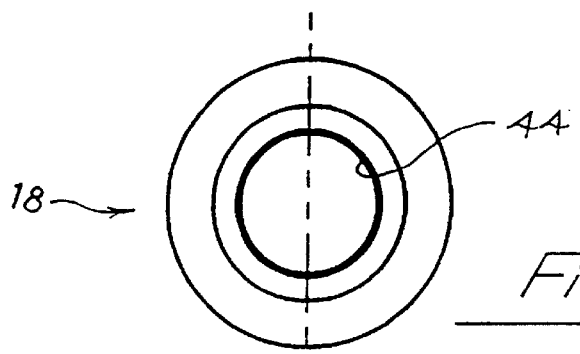

FIGS. 2 through 23 relate to a second preferred embodiment of a device for collecting and drying a body fluid such as blood. As shown in FIG. 2, the device 10 includes a housing 12 that is made up of an upper part 14 (FIGS. 5–12), a lower part 16 (FIGS. 13–19), and a plug 18 (FIGS. 20–22).

As best shown in FIG. 2, the upper part 14 defines an external opening 20 centered within a recess 22. The external opening 20 is aligned with an axis A, and the opening 20 provides fluid communication between the exterior of the housing 12 and a channel 24. The channel 24 is oriented substantially transversely to the axis A in this embodiment. In other embodiments, the channel 24 can be oriented at other nonparallel angles with respect to the axis A. The channel 24 provides a fluid flow path from the external opening 20 to an internal compartment 26 that is laterally offset from the external opening 20. The upper part 14 defines first and second openings 28, 30 that are in fluid communication with the internal compartment 26. First and second ribs 32, 34 extend around the internal compartment 26, the channel 24 and the external opening 20.

The lower part 16 defines first and second recesses 36, 38 positioned and sized to receive the first and second ribs 32, 34, respectively. The lower part 16 also defines three legs 40. These legs 40 extend downwardly from the lower surface of the lower part 16 and provide stable support for the device 10. The lower part 16 also defines a cylindrically shaped socket 42 that is in fluid communication with the internal compartment 26.

The plug 18 is sized to fit within the socket 42 in a press fit such that the plug 18 can be inserted into and removed from the housing 12 in a convenient manner. The plug 18 defines a central passageway 44 that is in fluid communication with the internal compartment 26. In this preferred embodiment, the plug 18 defines a slightly enlarged distal end and the socket 42 defines a slightly enlarged internal end. These features provide increased retention forces tending to hold the plug 18 in place when the plug 18 is fully inserted into the socket 42. Other retention methods may be used, including for example screw threads, bayonet locks, splines, snap fits, and the like.

As best shown in FIGS. 3–4, various membranes are mounted in the internal compartment 26. The upper part 14 defines a ledge 46 adjacent to the first opening 28, and the plug 18 defines a ledge 48 adjacent to the central passageway 44. The ledges 46, 48 retain the porous sheets described below in position in the internal compartment 26.

In particular, a vapor-permeable, liquid-barrier layer such as a porous hydrophobic membrane 50 is positioned immediately adjacent to the ledge 46, and a vapor-permeable, liquid-barrier layer such as a porous hydrophobic membrane 52 is positioned immediately adjacent to the ledge 48. The ledges 46, 48 hold the membranes 50, 52 in place during use.

In the embodiment of FIGS. 3–4, three sheets of porous material are mounted in the internal compartment 26 between the hydrophobic membranes 50, 52. These three sheets include a blood transport membrane 54, a blood separation membrane 56, and a serum collection membrane 58. The blood transport membrane 54 transports the selected body fluid (blood in this example) across the entire area of the internal compartment 26, and the blood transport membrane 54 is in fluid communication with the channel 24. The blood separation membrane 56 operates as a filter that separates blood cells from blood serum. The serum collection membrane 58 is positioned on the opposite side of the blood separation membrane 56 from the channel 24.

The device 10 is assembled by first placing the hydrophobic membrane 50, the blood transport membrane 54, and the blood separation membrane 56 in the compartment-defining recess of the upper part 14. Then the lower part 16 is assembled to the upper part 14. As shown in FIGS. 2 and 3, the lower part 16 locks the blood separation membrane 56 in place, thereby restraining any of the membranes 50, 54, 56 from moving out of the internal compartment 26 as long as the upper and lower parts 14, 16 remain in an assembled condition. The upper and lower parts 14, 16 can be held together by any suitable method, including a mechanical press fit, a mechanical welding or heat sealing operation, or an adhesive bonding operation.

Once the upper and lower parts 14, 16 have been assembled as described above, the plug 18 carrying the serum collection membrane 58 and the hydrophobic membrane 52 is positioned in the socket 42, thereby closing the internal compartment 26.

In use of the device 10, a drop of body fluid such as blood is introduced into the recess 22. The walls of the channel 24 are preferably formed of a material that facilitates capillary flow, and the channel 24 therefore conducts body fluid such as blood from the external opening 20 to the internal compartment 26, where the body fluid is introduced onto the blood transport membrane 54. Serum from the blood then passes through the blood separation membrane 56 (which blocks the flow of blood cells), and serum is collected on the collection membrane 58. The porous hydrophobic membranes 50, 52 allow vapor to escape from the internal compartment 26 while preventing the movement of blood out of the internal compartment 26. Once the membranes 54, 56 are saturated with blood, the capillary action ceases and no further blood is transported into the internal compartment 26 by the channel 24. As vapor leaves the internal compartment by the porous hydrophobic membranes 50, 52, the blood sample, including the serum collected on the serum collection membrane 58, dries. The user can see a reddening of the blood separation membrane 56 through the second opening 30 to confirm proper operation of the device 10.

Once the blood sample has dried, the plug 18 can be removed from the socket 42, thereby removing the serum collection membrane 58 from the internal compartment 26 for analysis. The dried serum sample can then be analyzed in any desired manner.

It will be seen that the device 10 can be used in a manner similar to the device 8 of FIG. 1(d), and the materials and analysis techniques described in connection with the device 8 can be used with the device 10.

Simply by way of example, the following preferred materials and dimensions can be used. It should be understood that the present invention is not limited to the specific details of construction described below.

By way of example, the internal compartment 26 can define a volume less than 1 ml and the channel 24 can define a cross-sectional dimension of less than 3 mm. The porous element in the embodiment described above substantially fills the entire internal compartment 26. In alternative embodiments, the porous element in a dry state fills at least 20% of the volume of the internal compartment 26. The channel 24 may be left empty of any absorbent material; alternately an absorbent material may be placed in the channel 24.

Table 1 provides examples of materials that can be used for the membranes 50 through 58.

TABLE 1

| Preferred Materials | |
|---|---|
| Reference No. | Preferred Membrane Material |
| 50, 52 | Ultra-high-hydrophobic-molecular weight, polyethylene filter with median pore size of 7 microns (e.g. Porex Technologies 7744) |
| 54, 58 | High density polyethylene filter with pore size of 80–120 microns (e.g. Porex Technologies X4588) |

TABLE 1-continued

Preferred Materials

| Reference No. | Preferred Membrane Material |
|---|---|
| 56 | Borosilicate microfiber glass filter with acrylic binder resin (e.g. Millipore AP20 and AP25) |

In one embodiment an additional filter membrane such as a reinforced mixed cellulose esters filter (e.g. Millipore AW19) is placed between the membranes 56 and 58.

Table 2 provides examples of dimensions that can be used for the device 10.

TABLE 2

Preferred Dimensions

| Feature | Dimension (mm unless otherwise indicated) |
|---|---|
| Diameter of opening 20 | 1.6 |
| Length of channel 24 | 2.5 |
| Width of channel 24 | 1.6 |
| Height of channel 24 | 1.4 |
| Diameter of membranes 50, 54 | 6.3 |
| Diameter of membrane 56 | 8.4 |
| Diameter of membranes 52, 58 | 6.3 |
| Distance between ledges 46, 48 | 4.1 |
| Volume of compartment 26 | 124 mm$^3$ |

The upper and lower parts 14, 16 and the plug 18 can be injection molded if desired from many suitable material. As described above, the selected material should provide the capillary action described above that draws blood from the external opening 20 via the channel 24 to the internal compartment 26. The following materials are believed suitable: ABS (e.g. Bayer Lustran ABS 243) or polyethylene (e.g. Phillips Marlex PE HHM 5502 BN).

Figure 23:
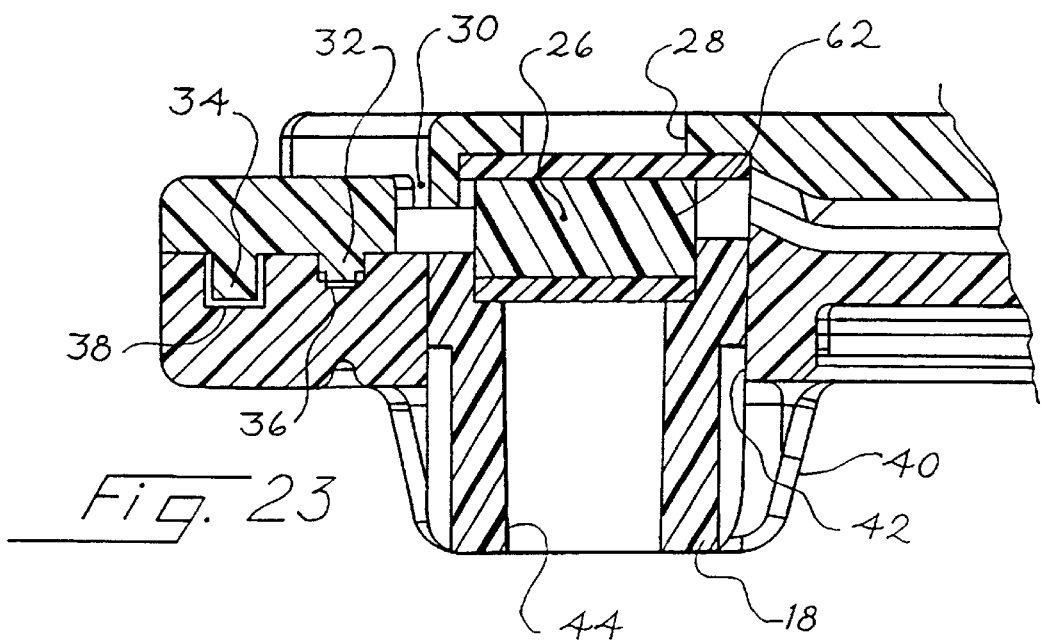
FIG. 23 is a fragmentary cross-sectional view of an alternative version of the device of FIGS. 2 through 4.

The membranes 54, 56, 58 taken together make up a porous element 60 disposed in the internal compartment 26. In an alternate embodiment, the sheets of porous material 54, 56, 58 can be replaced with a single porous element 62, as shown in FIG. 23. In this alternative, the device does not separate blood serum from blood cells, but rather dries the unseparated blood in the porous element 62. The device of FIG. 23 is identical to the device of FIG. 2, except for the porous element 62. For this reason, comparable reference numerals have been used in FIG. 23 and in FIG. 3.

The blood transport membrane, the blood separation membrane 56 and the serum collection membrane 58 are preferably formed of hydrophilic media that can uniformly absorb and distribute a fluid such as wet blood. The absorbent material used for the serum collection membrane 58 and the porous element 62 can allow for the non-covalent capture and binding of clinical chemistry analytes and their subsequent drying and elution, all the while maintaining their composition and integrity. The materials described above in conjunction with the device 8 can be used for the porous element 62.

The devices 8, 10 provide the advantage of collecting a well-controlled volume of blood. This precision of collection allows for more accurate and precise analytical determination of clinical chemistry analytes. The dried blood sample can be kept inside the devices 8, 10 at ambient temperatures and sent to a laboratory for testing.

Because the devices 8, 10 allow one to easily collect a defined volume of blood in the dried blood sample, even an untrained user can precisely and consistently collect samples for testing that are of optimum quality and quantity for accurate and precise analytical analysis.

Another advantage of the devices 8, 10 is that once the blood sample is inside the apparatus there is a lowered chance of contamination or loss of integrity of the sample. The housings protect the sample from being contaminated or physically compromised.

As used herein, the term "membrane" is intended broadly to encompass a wide variety of porous materials, including but not limited to membrane filters, depth filters, and various porous sheet materials.

It will be appreciated that the scope of this invention is to be defined by the claims appended hereto rather than the specific embodiments which have been presented herein by way of example.

What is claimed is:

1. A device for collecting and drying a body fluid, said device comprising:
    a housing forming an external opening, an internal compartment, and a channel extending between the external opening and the internal compartment;
    a water-permeable porous element disposed in the internal compartment for receiving the body fluid into the channel, and
    at least one vapor-permeable, liquid-barrier layer forming a boundary of the internal compartment.

2. The device of claim 1 wherein the internal compartment defines a volume less than 1 ml.

3. The device of claim 2 wherein the porous element in a dry state fills at least 20% of the volume.

4. The device of claim 1 wherein the channel defines a maximal cross sectional dimension less than 3 mm.

5. The device of claim 1 wherein the vapor-permeable, liquid-barrier layer is mounted to the housing adjacent to the internal compartment.

6. The device of claim 1 wherein the external opening is laterally offset from the internal compartment by the channel.

7. The device of claim 1 wherein the external opening defines an opening axis, and wherein the channel is oriented at a non-parallel angle to the opening axis.

8. The device of claim 1 wherein the external opening defines an opening axis, and wherein the channel is oriented substantially transverse to the opening axis.

9. The device of claim 1 wherein the housing comprises:
    a socket in communication with the internal compartment; and
    a plug removably disposed in the socket, removal of said plug from said socket providing access to the internal compartment.

10. The device of claim 9 wherein the plug forms a central passageway in communication with the internal compartment.

11. The device of claim 1, 5 or 10 wherein the porous element comprises a plurality of sheets of porous material.

12. The device of claim 11 wherein the sheets of porous material are operable to separate blood cells from blood serum.

13. The device of claim 11 wherein the sheets of porous material comprise a filter sheet and at least one additional sheet, wherein the at least one additional sheet is positioned on a first side of the filter sheet, and wherein the channel is positioned to introduce body fluid into the compartment on a second side of the filter sheet, opposite the first side.

14. The device of claim 1 further comprising a wicking element disposed in the channel.

15. The device of claim 14 wherein the wicking element is in one piece with the porous element.

16. The device of claim 1 wherein the porous element comprises a single water permeable element.

17. The device of claim 1 or 9 wherein the housing additionally comprises an additional opening in communication with the internal compartment on a side of the internal compartment opposite the channel.

18. The device of claim 17 wherein the additional opening is positioned to allow viewing of a portion of the porous element.

19. The device as claimed in claim 1 wherein each vapor-permeable, liquid-barrier layer comprises a porous, hydrophobic material.

20. The device as claimed in claim 1 wherein each vapor-permeable, liquid-barrier layer is water-impermeable.

21. The device as claimed in claim 1 wherein the channel defines a length between the external opening and the internal compartment and a maximum width transverse to the length, and wherein the length is greater than the width.

22. The device as claimed in claim 1 wherein the channel forms a capillary tube operative to conduct blood from the opening to the internal compartment.

* * * * *